(12) United States Patent
Lipkowski et al.

(10) Patent No.: US 8,084,429 B2
(45) Date of Patent: Dec. 27, 2011

(54) COMPOUNDS AND THEIR ANALGESIC APPLICATIONS

(76) Inventors: Andrzej Lipkowski, Warszawa (PL); Daniel Carr, Chesnut Hill, MA (US); Iwona Bonney, Somerville, MA (US); Dariusz Kosson, Warsawa (PL); Aleksandra Misjecka-Kesik, Piastow (PL)

( * ) Notice: Subject to any disclaimer, the term of this patent is extended or adjusted under 35 U.S.C. 154(b) by 148 days.

(21) Appl. No.: 10/524,343

(22) PCT Filed: Aug. 7, 2003

(86) PCT No.: PCT/PL03/00077
§ 371 (c)(1),
(2), (4) Date: Jan. 30, 2006

(87) PCT Pub. No.: WO2004/014943
PCT Pub. Date: Feb. 19, 2004

(65) Prior Publication Data
US 2006/0241053 A1     Oct. 26, 2006

(30) Foreign Application Priority Data
Aug. 13, 2002   (PL) .......................................... 355470

(51) Int. Cl.
*A61K 38/08* (2006.01)
*C07K 7/00* (2006.01)
*C07K 7/06* (2006.01)

(52) U.S. Cl. ...... 514/18.3; 514/1.1; 514/18.4; 514/21.7; 530/300; 530/328

(58) Field of Classification Search .......................... None
See application file for complete search history.

(56) References Cited

U.S. PATENT DOCUMENTS
5,356,902 A * 10/1994 Ornstein ..................... 514/307
5,880,132 A *  3/1999 Hill ............................. 514/282

FOREIGN PATENT DOCUMENTS
EP         0 434 369 A1 *  6/1991

OTHER PUBLICATIONS

Lipkowski et al., "Biological Activity of Fragments and Analogues of the Potent Dimeric Opioid Peptide Biphalin," Biorg. Med. Chem. Let., 1999, 9, 2763-6.*

Ronai et al., "Tetrapeptide-amide analogs of enkephalin: the role of the C-terminus in determining the character of opioid activity," Biochem. Biophys. Res. Comm., 1979, 91, 1239-49.*

Abbruscato et al., "Brain and Spinal Cord Distribution of Biphalin: Correlation with Opioid Receptor Density and Mechanism of CNS Entry," J. Neurochem., 1997, 69, 1236-45.*

Kanai et al. "Expression Cloning and Characterization of a Transporter for Large Neutral Amino Acids Activated by the Heavy Chain of 4F2 Antigen (CD98)," J. Biol. Chem., 1998, 273, 23629-32.*

Lipkowski, A. W. et al. (2002) "Biological properties of a new fluorescent biphalin fragment analogue." *Life Sciences*, vol. 70, No. 8, pp. 893-897.

* cited by examiner

*Primary Examiner* — Julie Ha
(74) *Attorney, Agent, or Firm* — Gary J. Gershik; Cooper & Dunham LLP

(57) ABSTRACT

Provided are compounds represented by:

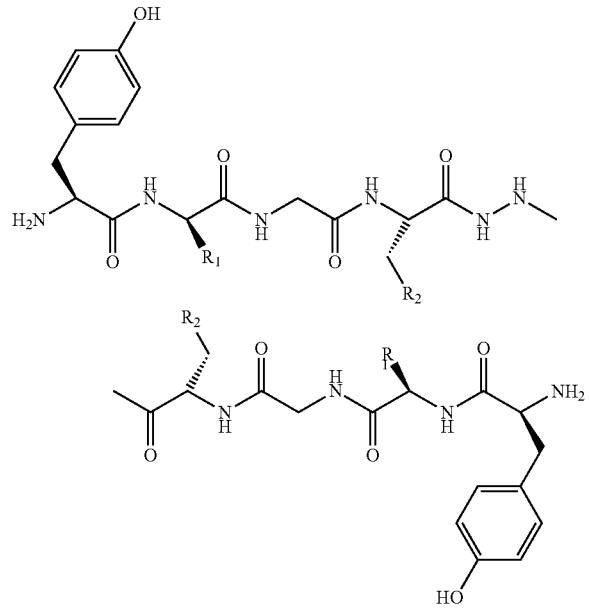

wherein $R_1$ is a D-alanine, D-serine, D-threonine, D-methionine, D-leucine, D-asparagine or D-glutamine side chain and $R_2$ is a phenylalanine or tryptophan side-chain, and compositions containing such compounds.

20 Claims, 2 Drawing Sheets

R₁ = D-Ala or D-Ser or D-Thr or D-Met or D-Leu or D-Asn or D-Gln
R₂ = Phe or Trp

COMPOUNDS AND THEIR ANALGESIC APPLICATIONS

This application is a §371 national phase of PCT International Application No. PCT/PL2003/000077, filed Aug. 7, 2003, which claims priority of Polish application No. P.355470, filed Aug. 13, 2002.

FIELD OF THE INVENTION

The present invention relates to the application of peptides with analgesic properties as the active ingredients to be used in techniques of direct application of medicaments to putative sites of analgesic activity, particularly in the central nervous system.

BACKGROUND OF THE INVENTION

Pain and its alleviation are some of the most important challenges of modern medicine. During the last several decades a great deal of progress has been made in the design of new medications and methods of their administration. The most popular methods of administering the medication to a patient are oral, topical and intramuscular. Analgesics administered in these ways must have a high degree of specificity, as well as pharmacological properties which guarantee easy penetration of biological barriers such as the skin-circulatory system barrier, the intestine-blood barrier and the brain-blood barrier. Such compounds disperse throughout the organism after application, including the central nervous system, where preferentially they block the transmission of pain stimuli through the spinal cord and the perception of pain in the brain. The arsenal of systemic application techniques of analgesics was enriched in the last few years by modern methods of administering the medication directly to those structures where preferentially it is expected that it would act on the receptors participating in the dampening or generation of pain signals. The medication may be introduced in the form of a physiological saline solution, using a syringe extended with a catheter introduced to the destination site of the medication. The syringe can be replaced with a variety of infusion pumps allowing the constant introduction of the medication over time, and/or allowing the doctor and/or the patient to control the dose of medication administered. Descriptions of the techniques and devices in questions are well presented in the work by D. B. Carr and M. J. Cousins entitled "Spinal route of Analgesia. Opioids and future options", which is a chapter in "Neuronal blockade in clinical anesthesia and management of pain" (ed. M. J. Cousins and P. O. Bridenbaugh), published by Lippincott-Raven Press, Philadelphia, 1998, pp. 915-983. The chief target of analgesic medication are receptors in the central nervous system, particularly in the spinal cord. In the last years, however, the presence receptors modulating pain stimuli has also been noted at sites of tissue damage. That is why independently of central nervous system analgesia, local application at post-operative sites is also practised. In all these modern medication application techniques traditional analgesic preparations are used, such as morphine or phentanyl. Such compounds are characterised by high biological barrier permeability, thus their efficacy in local application is limited.

In 1986, Andrzej W. Lipkowski was granted Polish Patent No. 131730 for "A Method for the Production of Peptides with Morphine-like Activity". This patent also describes the synthesis of a compound with the structure presented in FIG. 1. This compound has the common name of biphaline. Investigations of biphaline have shown that this compound has an analgesic activity level similar to morphine when introduced intravenously. Following direct administration to the central nervous system, analgesic activity of the compound was noted, but the level of this activity was variously interpreted by researchers.

The purpose of this invention is to deliver new compounds, which could be utilised to obtain better analgesic agents, particularly for direct local administration, which would at the same time show high anaesthetic activity and were denuded of the known unwanted side effects of opiate compounds, such as the ability to cause respiratory depression.

It was unexpectedly shown that this problem can be solved by the present invention.

SUMMARY OF THE INVENTION

The present invention relates to a compound with the formula shown in FIG. 2, where preferentially R1 means an amino acid residue of D-alanine, D-serine, D-threonine, D-methionine, D-leucine, D-asparagine or D-glutamine, whereas R2 means an amino acid residue of phenyloalanine or tryptophan. Preferentially, this compound is a peptide selected from among:

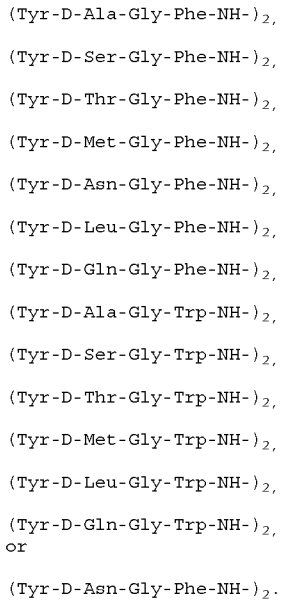

(Tyr-D-Ala-Gly-Phe-NH-)$_2$, (Tyr-D-Ser-Gly-Phe-NH-)$_2$, (Tyr-D-Thr-Gly-Phe-NH-)$_2$, (Tyr-D-Met-Gly-Phe-NH-)$_2$, (Tyr-D-Asn-Gly-Phe-NH-)$_2$, (Tyr-D-Leu-Gly-Phe-NH-)$_2$, (Tyr-D-Gln-Gly-Phe-NH-)$_2$, (Tyr-D-Ala-Gly-Trp-NH-)$_2$, (Tyr-D-Ser-Gly-Trp-NH-)$_2$, (Tyr-D-Thr-Gly-Trp-NH-)$_2$, (Tyr-D-Met-Gly-Trp-NH-)$_2$, (Tyr-D-Leu-Gly-Trp-NH-)$_2$, (Tyr-D-Gln-Gly-Trp-NH-)$_2$,
or (Tyr-D-Asn-Gly-Phe-NH-)$_2$.

This invention also relates to an analgesic agent containing an active ingredient and possibly a pharmaceutically acceptable diluent or filler, characterised in that as the active ingredient it contains a compound described above. An analgesic agent according to this invention can also contain another active ingredient, particularly a compound selected from among compounds blocking stimulatory amino acid receptors, compounds blocking tachykinin receptors, as well as compounds blocking cholecystokinin receptors. In a particular embodiment, the analgesic agent according to the present invention is a solution in an aqueous physiological saline solution. The analgesic agent according to the present invention can be meant for direct application to the site of the desired analgesic activity, particularly as a constant application or infusion. In a particular embodiment of the invention, such an analgesic agent is meant for direct application to the appropriate site of the central nervous system. In one of the considered embodiments, the analgesic agent according to the present invention contains biphaline as an active ingredient.

The present invention also relates to the application of the compound defined above according to the present invention in the production of an analgesic medication. In particular, for the production of the medication one also utilises a compound selected from among compounds blocking stimulatory amino acid receptors, compounds blocking tachykinin receptors, as well as compounds blocking cholecystokinin receptors.

The present invention also relates to a method for the deadening of pain, characterised in that the patient requiring this is given an analgesic agent containing a compound according to the present invention described above, where preferentially preferentially it is applied directly to the site of the desired analgesic activity. Preferentially, the analgesic agent is applied directly to an appropriate site in the central nervous system. In particular, the administered analgesic agent contains biphaline. Also preferentially, the administered analgesic agent contains a compound selected from among compounds blocking stimulatory amino acid receptors, compounds blocking tachykinin receptors, as well as compounds blocking cholecystokinin receptors. In a method according to the present invention, the analgesic agent may be administered in a constant or periodic fashion, and may particularly be administered as a local infusion.

DETAILED DESCRIPTION OF THE INVENTION

Figure 1:
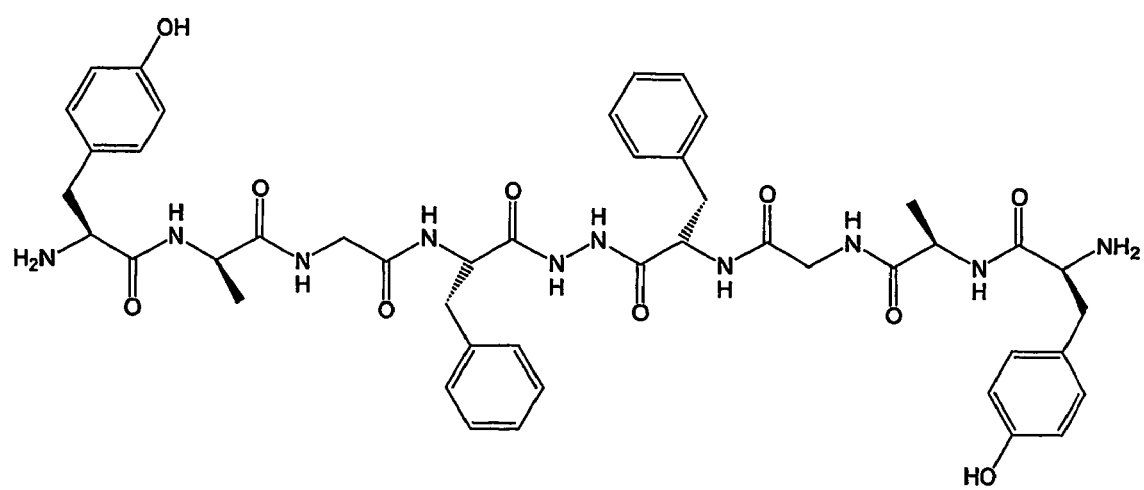
FIG. 1: A formula for biphaline.
Figure 2:
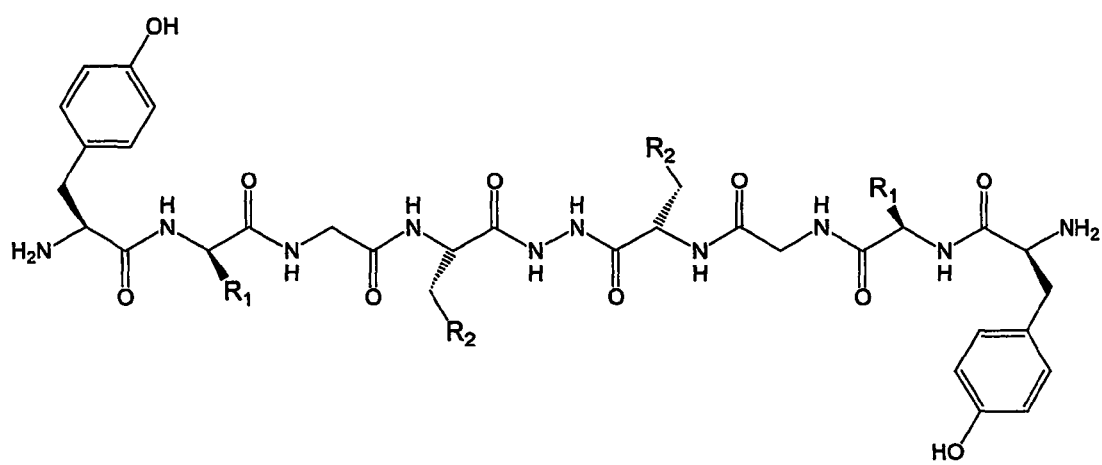
FIG. 2: A general formula of biphaline analogues according to the present invention.

When under stringent administration site control, it was unexpectedly shown that biphaline administered intrathecally is approximately a thousand times more effective as an analgesic than morphine, which was used as a reference compound. It was also noticed that biphaline analogues with sequences listed in Table 1 exhibited strong analgesic practivities comparable to biphaline. It was also unexpectedly shown that biphaline and its analogues administered at extremely high dosages, as much as a thousand-fold the minimal effective analgesic dose, did not cause respiratory depression, which is a significant undesirable effect of morphine and other analgesics currently in use. The biological properties of biphaline and its analogues, such as its anaesthetic activity, as well as a wide safety margin, as well as low permeability through biological barriers predispose these compounds for use as the active ingredients in devices for the application of biologically active compounds directly to the expected site of their activity in the central nervous system.

The application of peptides with analgesic activity as the active ingredient in devices for the application of biologically active compounds directly to the expected site of their analgesic activity according to the present invention, consists of a solution of biphaline or its analogue, or these compounds in conjunction with antagonists of tachykinin, or antagonists of cholecystokinin or antagonists of stimulatory amino acids, being the cargo of a device for the administration of a medication directly to the expected site of their analgesic activity, including the intrathecal space of animals, preferentially mammals or humans, where the devices may be a syringe designed for epidural injection, or another, automatic device for delivery of medication to the central nervous system or one which possesses the capability of dosage control by the patient and/or the medical service.

The table below presents the sequences of selected peptides according to the present invention, which are described in detail in the following examples.

TABLE I

The amino-acid sequences of the peptides studied, whose anaesthetic activity at a dose of 0.05 micrograms, was greater than 50% MPE after 15 minutes following administration, when given intrathecal to a rat.

| | |
|---|---|
| 1. | (Tyr-D-Ala-Gly-Phe-NH-)$_2$ |
| 2. | (Tyr-D-Ser-Gly-Phe-NH-)$_2$ |
| 3. | (Tyr-D-Thr-Gly-Phe-NH-)$_2$ |
| 4. | (Tyr-D-Met-Gly-Phe-NH-)$_2$ |
| 5. | (Tyr-D-Asn-Gly-Phe-NH-)$_2$ |
| 6. | (Tyr-D-Leu-Gly-Phe-NH-)$_2$ |
| 7. | (Tyr-D-Gln-Gly-Phe-NH-)$_2$ |
| 8. | (Tyr-D-Ala-Gly-Trp-NH-)$_2$ |
| 9. | (Tyr-D-Ser-Gly-Trp-NH-)$_2$ |
| 10. | (Tyr-D-Thr-Gly-Trp-NH-)$_2$ |
| 11. | (Tyr-D-Met-Gly-Trp-NH-)$_2$ |
| 12. | (Tyr-D-Leu-Gly-Trp-NH-)$_2$ |
| 13. | (Tyr-D-Gln-Gly-Trp-NH-)$_2$ |
| 14. | (Tyr-D-Asn-Gly-Phe-NH-)$_2$ | where individual amino acid residues are marked in three-letter codes: Tyr denotes L-tyrosine, D-Ala denotes D-alanine, D-Ser denotes D-serine, D-Thr denotes D-threonine, D-Met denotes D-methionine, D-Asn denotes D-asparagine, D-Gln denotes D-glutamine, Gly denotes glycine, Phe denotes L-phenyloalanine.

A solution of biphaline or its analogue according to the present invention may be a solution in a physiological saline, containing or not containing additional substances enhancing the analgesic activity. Among substances enhancing the analgesic activity of biphaline according to the present invention one may include NMDA antagonists and/or tachykinin antagonists and/or cholecystokinin antagonists.

The following examples will illustrate the invention further. These examples are however in no way intended to limit the scope of the present invention as obvious modifications will be apparent, and still other modifications and substitutions will be apparent to anyone skilled in the art.

EXAMPLE I

A silicone catheter was introduced into the intrathecal space of a rat in the cervical region of the spine, having an external diameter of 0.64 mm and an internal diameter of 0.3 mm. The 12 cm long catheter was prepared in the following way: at a distance of 7.5 cm from the end of the catheter, a flange was made around it with soft silicone glue. The remaining 4.5 cm stretch of the catheter was extended to the outside and connected to a 30G needle mounted on a 25 microliter Hamilton syringe. The implantation of the catheter was made under general anaesthesia. After shaving the coat from the shoulders and neck, the rat was placed in a stereotactic apparatus. The 1.5 cm long incision was made centrally, front to rear, along the axis of the spine. After reaching the muscles, they were prised apart and access to the basal membrane was prepared. The basal membrane was incised. The prepared catheter, filled with a sterile physiological saline solution, was inserted the through the incision in the membrane to a depth of 7.5 cm towards the rear, so that its end was found at the location of the L1. The muscle and skin were sutured. After recovery from general anaesthesia the rats were placed in separate cages. Biphaline was administered and measurements were made during the second day following the operation. All epidural injections were made at a constant volume of 10 microliters. Following the injection, the catheter was rinsed with 15 microliters of sterile physiological saline solution. Analgesis was measured in relation to a tail retraction test to which a thermal stimulus was applied in the form of a beam of light with a temperature of 55° C. The temperature and focus of the light was such that the time of reaction of the rat fit within the 2-3 second margin. The maximum time that the tail was agitated with the pain-stimulating light stimulus was set as 7 seconds, so as not to cause tail burns connected with a prolonged exposure of tissues to temperature. The pain-stimulating stimulus threshold was determined previous to administration of the compounds, as well as at the 5, 15, 30, 60 and 120 minutes following the administration. The degree of analgesis was expressed as a percent of the maximum possible effect (denoted as % MPE) according to the following equation:

$$\% \; MPE = \frac{T(5-120) - T(0)}{7 - T(0)} \times 100$$

where T(0) is the reaction time before administration of the compound; T(5-120) is the reaction time in the appropriate interval, and 7 is a time constant.

Following the procedure, the localisation of the catheter and the extent of its reach were determined using spinal radiography following an injection of lead acetate solution. Analysis was performed only on those animals with the catheter inserted correctly.

The analgesic activity of biphaline was observed with a minimal dose of 0.005 micrograms. The anaesthetic effect was 68% MPE in the $5^{th}$ minute, growing to 74% MPE in the 15th minute, to slowly decline to 30% MPE in the $30^{th}$ minute. After an hour, sensitivity to the thermal stimulus returned to normal.

EXAMPLE II

The experiment was performed in conditions identical to Example I, except that the dose was adjusted to 0.5 micrograms of biphaline. The anaesthetic effect obtained was respectively 90% MPE 5 minutes following the administration, 98% MPE 15 minutes following the administration, 100% MPE 30 minutes following the administration, 70% 1 hour following the administration, and 27% MPE two minutes following the administration. No undesirable effects were observed.

EXAMPLE III

The experiment was performed in conditions identical to Example I, except that the active ingredients were biphaline, at a dose of 0.005 micrograms as well as ketamine at a dose of 100 micrograms. The anaesthetic effect obtained was respectively 100% MPE after 5 minutes, 100% MPE after 15 minutes, 98% MPE after 30 minutes, 52% MPE after 1 hour and 8% MPE after 2 hours following the administration of the compounds. No undesirable effects were observed.

EXAMPLE IV

The experiment was performed in conditions identical to Example I, except that the active substance was a biphaline analogue (Tyr-D-Thr-Gly-Phe-NH—)$_2$ at a dose of 0.05 micrograms. The anaesthetic effect obtained was respectively 100% MPE after 5 minutes, 78% MPE after 15 minutes, 41% after 30 minutes and 10% MPE after 1 hour following the administration of the active ingredients. No undesirable effects were observed.

EXAMPLE V

The experiment was performed in conditions identical to Example I, except that the active ingredient was the biphaline analogue (Tyr-D-Gln-Gly-Phe-NH—)$_2$ at a dose of 0.05 micrograms. The anaesthetic effect obtained was respectively 100% MPE after 5 minutes, 68% MPE after 15 minutes, 50% after 30 minutes and 18% MPE after 1 hour following the administration of the active ingredients. No undesirable effects were observed.

EXAMPLE VI

The experiment was performed in conditions identical to Example I, except that the active ingredient was a biphaline analogue (Tyr-D-Met-Gly-Phe-NH—)$_2$ at a dose of 0.05 micrograms. The anaesthetic effect obtained was respectively 100% MPE after 5 minutes, 98% MPE after 15 minutes, 80% after 30 minutes and 42% MPE after 1 hour following the administration of the active ingredients. No undesirable effects were observed.

EXAMPLE VII

The experiment was performed in conditions identical to Example I, except that the active ingredient was a biphaline analogue (Tyr-D-Leu-Gly-Trp-NH—)$_2$ at a dose of 0.05 micrograms. The anaesthetic effect obtained was respectively 100% MPE after 5 minutes, 100% MPE after 15 minutes, 62% after 30 minutes and 30% MPE after 1 hour following the administration of the active ingredients. No undesirable effects were observed.

EXAMPLE VIII

The experiment was performed in conditions identical to Example I, except that the dose under study was 25 micrograms of biphaline. After three minutes following the injection stiffness of limb and back muscles was observed, while respiratory ability was maintained. The stiffness was maintained for 4 hours, and for the next three hours the animal did not react to any pain stimuli. After another 2 hours, the anaesthetic effect described in the study in Example I was 80% MPE. After 12 hours the animal's pain response and behaviour were normal.

EXAMPLE IX

The experiment was performed in conditions identical to Example I, except that after a single administration of 0.005 micrograms of biphaline, 0.003 micrograms of biphaline were administered after 0.5 hours, and the administration of 0.003 micrograms of biphaline every half hour was continued for 8 hours. Anaesthesia was measured in 1 hour intervals. It was noted that the anaesthetic effect was maintained throughout the duration of the experiment at a level of 80% MPE. No undesirable effects were observed.

The invention claimed is:
1. A compound represented by the formula:

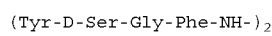

```
(Tyr-D-Met-Gly-Phe-NH-)2

(Tyr-D-Leu-Gly-Phe-NH-)2

(Tyr-D-Gln-Gly-Phe-NH-)2

(Tyr-D-Ala-Gly-Trp-NH-)2

(Tyr-D-Ser-Gly-Trp-NH-)2

(Tyr-D-Thr-Gly-Trp-NH-)2

(Tyr-D-Met-Gly-Trp-NH-)2

(Tyr-D-Leu-Gly-Trp-NH-)2

(Tyr-D-Gln-Gly-Trp-NH-)2
or (Tyr-D-Asn-Gly-Phe-NH-)2,
``` wherein the compound has the structure

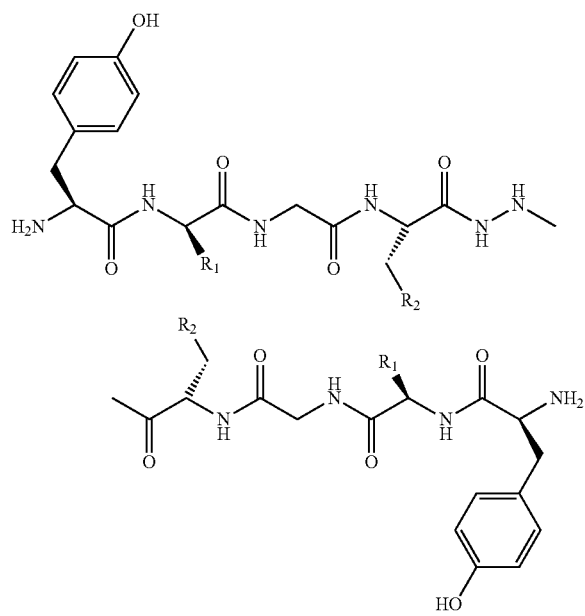

wherein $R_1$ is a D-alanine, D-serine, D-threonine, D-methionine, D-leucine, D-asparagine or D-glutamine side-chain and $R_2$ is a phenylalanine or tryptophan side-chain.

2. An analgesic medication containing the compound of claim 1 and a pharmacologically acceptable carrier.

3. The analgesic medication according to claim 2, further comprising a compound selected from a group consisting of compounds blocking stimulatory amino acid receptors, compounds blocking tachykinin receptors, and compounds blocking cholecystokinin receptors.

4. The analgesic medication according to claim 2, in the form of an aqueous physiological saline solution.

5. The analgesic medication according to claim 2, characterised in that it is designed for direct application to the site of the desired analgesic activity.

6. The analgesic medication according to claim 5, characterised in that it is designed for direct application to an appropriate site of the central nervous system.

7. The analgesic medication according to claim 6, further comprising biphaline.

8. A method of alleviating pain in a subject, comprising administering to the subject at the site of the pain a compound according to claim 1.

9. The method according to claim 8, wherein the compound is administered directly to the appropriate site of the central nervous system.

10. The method according to claim 8, further comprising administering biphaline.

11. The method according to claim 8, further comprising administering a compound selected from the group consisting of compounds blocking stimulatory amino acid receptors, compounds blocking tachykinin receptors, and compounds blocking cholecystokinin receptors.

12. The method according to claim 8, wherein the compound is administered constantly or periodically.

13. The method according to claim 8, wherein the compound is in the form of a solution and it is administered by local infusion.

14. The compound of claim 1, having the formula (Tyr-D-Met-Gly-Phe-NH—)$_2$.

15. The compound of claim 1, having the formula (Tyr-D-Gln-Gly-Phe-NH—)$_2$.

16. The compound of claim 1, having the formula (Tyr-D-Leu-Gly-Trp-NH—)$_2$.

17. The compound of claim 1, having the formula (Tyr-D-Ser-Gly-Phe-NH—)$_2$.

18. The compound of claim 1, having the formula (Tyr-D-Leu-Gly-Phe-NH—)$_2$.

19. The compound of claim 1, having the formula (Tyr-D-Ser-Gly-Trp-NH—)$_2$.

20. The compound of claim 1, having the formula (Tyr-D-Thr-Gly-Trp-NH—)$_2$.

* * * * *